(12) United States Patent
Danz et al.

(10) Patent No.: US 6,471,928 B1
(45) Date of Patent: Oct. 29, 2002

(54) AQUEOUS FORMALDEHYDE SOLUTIONS WITH A LOW TETROXANE CONTENT

(75) Inventors: Eckehard Danz, Ludwigshafen (DE); Klaus Pandl, Hambrücken (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/807,973

(22) PCT Filed: Oct. 14, 1999

(86) PCT No.: PCT/EP99/07744

§ 371 (c)(1),
(2), (4) Date: Apr. 27, 2001

(87) PCT Pub. No.: WO00/24699

PCT Pub. Date: May 5, 2000

(30) Foreign Application Priority Data

Oct. 27, 1998 (DE) .......................... 198 49 380

(51) Int. Cl.⁷ ............................ B01J 10/00; C09K 15/06
(52) U.S. Cl. ............................... 423/245.2; 423/245.1; 252/1; 252/182.23; 252/407; 252/364
(58) Field of Search .................. 252/1, 407, 182.23, 252/364; 568/855; 502/174; 423/245.1, 245.2

(56) References Cited

U.S. PATENT DOCUMENTS

| | | | |
|---|---|---|---|
| 1,481,849 A | | 1/1924 | Meyer |
| 3,920,390 A | * | 11/1975 | Petersen et al. .............. 8/185 |
| 3,985,696 A | * | 10/1976 | Aignesberger et al. |
| 4,003,846 A | * | 1/1977 | Kuhn et al. |
| 4,013,813 A | * | 3/1977 | LeBlanc et al. ............ 428/272 |
| 4,058,498 A | * | 11/1977 | Bonnet ........................ 252/8.8 |
| 4,219,508 A | * | 8/1980 | Wagner ....................... 568/387 |
| 4,526,606 A | * | 7/1985 | Formaini .......................... 71/3 |
| 4,584,418 A | | 4/1986 | Fremont |
| 4,960,856 A | * | 10/1990 | Formaini ..................... 528/256 |
| 4,968,772 A | * | 11/1990 | Whiteside .................... 528/230 |
| 4,996,289 A | * | 2/1991 | Berbner et al. ............. 528/230 |
| 5,017,641 A | * | 5/1991 | Kemptes et al. ............ 524/598 |

FOREIGN PATENT DOCUMENTS

| | | |
|---|---|---|
| GB | 931892 | 7/1963 |
| GB | 1 037 934 | 8/1966 |
| GB | 2 023 020 | 12/1979 |

OTHER PUBLICATIONS

Chemical Abstracts, JP 52–153905, 1977.

* cited by examiner

*Primary Examiner*—Joseph D. Anthony
(74) *Attorney, Agent, or Firm*—Oblon, Spivak, McClelland, Maier & Neustadt, P.C.

(57) ABSTRACT

The claimed invention relates to a process for preparing an aqueous formaldehyde solution comprising absorbing a formaldehyde-loaded gas stream, in an absorption zone, in an aqueous solution comprising from 0.000% to 0.01% by weight of a Bronsted base, based on the formaldehyde absorbed. The produced aqueous formaldehyde solution comprises: a) from 10 to 75% by weight of formaldehyde, b) from 0 to 500 ppm by weight of tetroxane, c) from 50 to 400 ppm by weight of formic acid, based on the formaldehyde absorbed, and d) from 0.2 to 5.0% by weight of methanol, based on the formaldehyde absorbed.

7 Claims, 1 Drawing Sheet

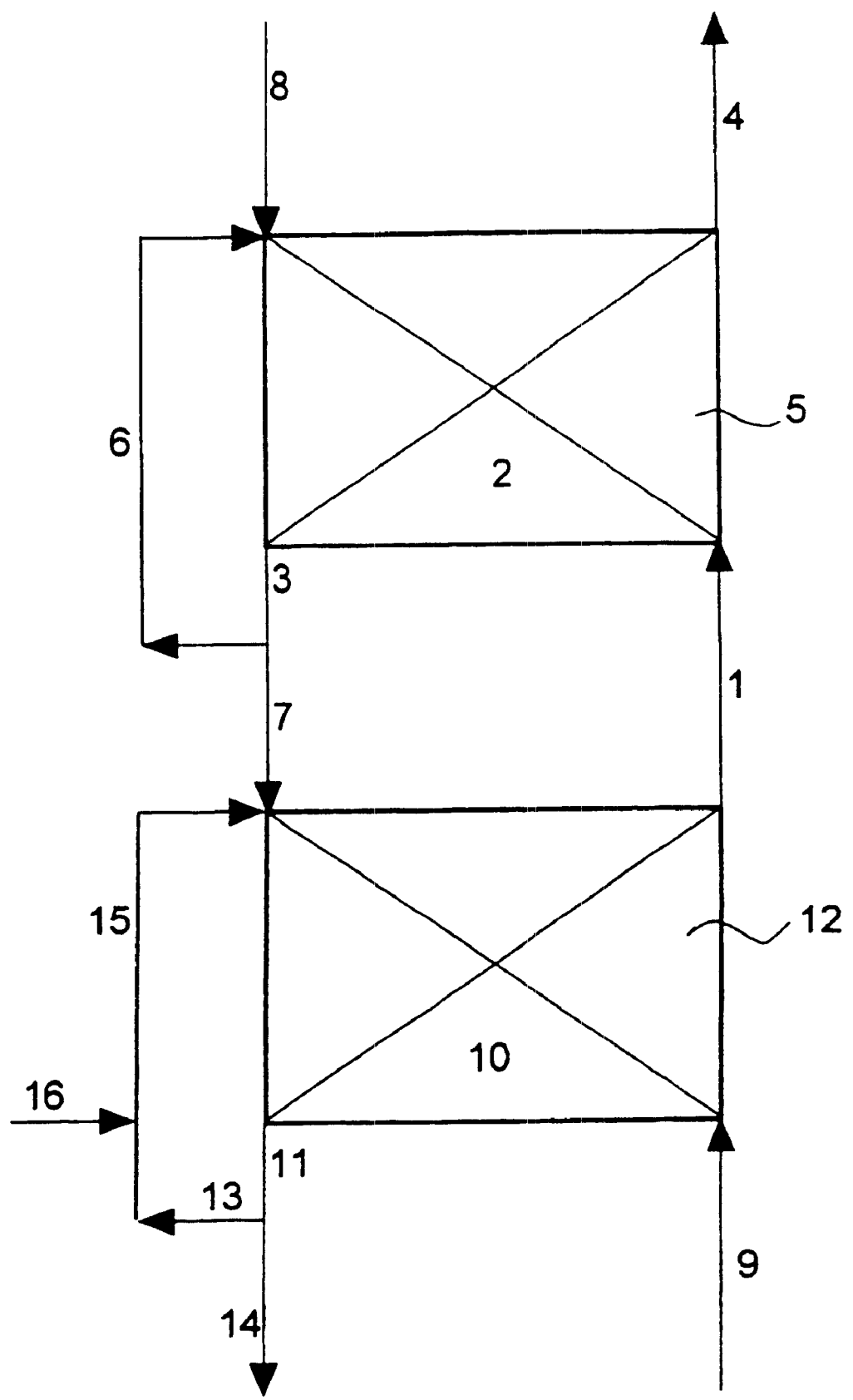

AQUEOUS FORMALDEHYDE SOLUTIONS WITH A LOW TETROXANE CONTENT

The invention relates to low-tetroxane aqueous formaldehyde solutions having a pH of from 3.4 to 4.2 comprising
 a) from 10 to 75% by weight of formaldehyde
 b) from 0 to 500 ppm by weight of tetroxane.

The invention further relates to processes for their preparation and to a process for preparing 1,4-butanediol by reacting the low-tetroxane aqueous formaldehyde solutions with acetylene to form 1,4-butynediol and subsequent hydrogenation of the 1,4-butynediol to form 1,4-butanediol.

Aqueous formaldehyde solutions and processes for their preparation are generally known (cf. Ullmanns Encyclopädie der technischen Chemie [Ullmann's Encyclopedia of Industrial Chemistry], Verlag Chemie, GmbH, Weinheim, 4th edition, volume 11, keyword formaldehyde, chapter 3).

For this purpose, generally, methanol is first dehydrogenated oxidatively with air and the formaldehyde-containing gas stream formed as a result is brought into contact with water in an absorption zone, an aqueous formaldehyde solution being formed.

However, the formaldehyde solutions formed in this process have the disadvantage that the formaldehyde partially reacts even within a very short time to form tetroxane of the formula (I)

(I)

so that, in concentrated formaldehyde solutions, frequently as soon as within one day after their preparation, several hundred ppm of tetroxane form.

Formaldehyde solutions are used as an intermediate in the synthesis of many chemical substances. In many cases here, the tetroxane is not reacted, but remains as residue in the waste water during the work up of the reaction mixture. Since tetroxane is categorized as a hazard to water according to relevant environmental directives, waste waters of this type must be freed from tetroxane by complex clean up operations. This problem arises, in particular, in the preparation of 1,4-butanediol by reacting the aqueous formaldehyde solutions with acetylene to form 1,4-butynediol and subsequent hydrogenation of the 1,4-butynediol to form 1,4-butanediol, the tetroxane being produced in a mixture with water and the product of value 1,4-butanediol.

It is an object of the present invention, therefore, to prepare aqueous formaldehyde solutions which, despite relatively long storage, comprise no, or only small amounts of, tetroxane.

We have found that this object is achieved by aqueous solutions of the type described at the outset, processes for their preparation and a process for preparing 1,4-butanediol using these solutions.

Since formaldehyde solutions are generally handled as solutions having a formaldehyde content of from 30 to 60% by weight, the preferred aqueous solutions according to the invention usually likewise comprise formaldehyde in these concentrations.

The aqueous solutions according to the invention generally comprise from 50 to 400, preferably from 50 to 300, ppm by weight of formic acid and from 0.2 to 5.0, preferably from 0.5 to 2.5, % by weight of methanol, since in the majority of industrial processes for preparing formaldehyde, the formaldehyde is produced in the form of formaldehyde-loaded gas streams which usually comprise
 from 5 to 30% by weight of formaldehyde
 from 0.5 to 2.0% by weight of methanol
 from 30 to 55% by weight of nitrogen
with or without traces of formic acid.

The industrial preparation of formaldehyde and aqueous formaldehyde solutions is generally known and is described, for example, in Ullmanns Encyclopädie der technischen Chemie [Ullmann's Encyclopedia of Industrial Chemistry], Verlag Chemie, GmbH, Weinheim, 4th edition, volume 11, keyword formaldehyde, chapter 3.

In the subsequent preparation of aqueous formaldehyde solutions by selective absorption of these formaldehyde-loaded gas streams in water, it is unavoidable that a certain proportion of methanol and formic acid is co-absorbed. In addition, in the storage of the solutions, methanol and formic acid are formed by disproportionation of formaldehyde. Tetroxane formation in these solutions may be effectively avoided or retarded by adjusting their pH to from 3.4 to 4.2.

This is achieved using Brönsted bases such as ammonia, an alkali metal hydroxide or an alkali metal carbonate. Generally, the aqueous formaldehyde solutions comprise from 0.001 to 0.1% by weight of the Brönsted base, based on the formaldehyde absorbed therein.

Expediently, a procedure is followed such that
 I. a formaldehyde-loaded gas stream is absorbed in water and
 II. in the course of 30 min after the absorption, from 0.001 to 0.1% by weight of a Brönsted base, based on the formaldehyde absorbed, is dissolved.

Particularly expediently, to prepare the solutions according to the invention, a procedure is followed such that the base is added as early as immediately after or during the preparation of the conventional formaldehyde solutions. This can be performed industrially, for example, by absorbing, in a plurality of absorption stages, in water or aqueous formaldehyde solutions, a reaction gas, such as is produced in the oxidative dehydrogenation of methanol by air on a silver catalyst, and adding the base to the absorption stage to which the reaction gas is fed directly.

BRIEF DESCRIPTION OF THE DRAWING

FIG. 1 is a schematic diagram of one variant of preparing aqueous formaldehyde solution according to the invention.

According to this variant, the formaldehyde solutions according to the invention are therefore prepared by:
 in a 1st absorption stage
  a part-formaldehyde-depleted gas stream I (1) being partially absorbed in a part-formaldehyde-loaded aqueous solution I (2), a part-formaldehyde-loaded aqueous solution II (3) and a formaldehyde-depleted gas stream II (4) having decreased formaldehyde content being formed, by conducting the part-formaldehyde-depleted gas stream I (1) and the part-formaldehyde-loaded aqueous solution I (2) in countercurrent through an absorption zone I (5),
  the formaldehyde-depleted gas stream II (4) and the part-formaldehyde-loaded aqueous solution II (3) being removed from the extraction zone I (5),
  the part-formaldehyde-loaded aqueous solution II (3) being divided into 2 partial streams I (6) and II (7),
  the partial stream I (6) being passed into the absorption zone I (5) together with an aqueous solution W (8)

which comprises no formaldehyde or smaller amounts thereof than the part-formaldehyde-loaded aqueous solution I (2), partial stream I (6) and the aqueous solution W together forming the part-formaldehyde-loaded aqueous solution I (2)

and in a further upstream absorption stage 2 a formaldehyde-loaded gas stream III (9) being partially or completely absorbed in a part-formaldehyde-loaded aqueous solution III (10), a formaldehyde-loaded aqueous solution IV (11), which solution IV is the desired product of value, and the part-formaldehyde-depleted gas stream I (1) being formed, by conducting the formaldehyde-loaded gas stream III (9) and the part-formaldehyde-loaded aqueous solution III (10) in countercurrent through an absorption zone II (12), the formaldehyde-loaded aqueous solution IV (11) and the part-formaldehyde-depleted gas stream I (1) being removed from the absorption zone II (12), the formaldehyde-loaded aqueous solution IV (11) being divided into 2 partial streams III (13) and IV (14), a partial stream V (15) being produced by adding from 0.001 to 0.01% by weight of a Brönsted base (16) to the partial stream III (13) per unit time and per part by weight of formaldehyde which is passed into the absorption zone II (12) in the form of the formaldehyde-loaded gas stream III (9) and the partial stream V (15) being passed together with partial stream II (7) together into the absorption zone II, partial stream V (15) and II (7) together forming the part-formaldehyde-loaded aqueous solution III (10).

This procedure is shown diagrammatically in FIG. 1.

In this process variant, the formaldehyde-loaded gas streams 3 in particular are used such as are formed in the industrial preparation of formaldehyde.

Expediently, 2 or 3 absorption stages of the type of absorption stage I are connected in series and, in the last absorption stage, as aqueous solution which comprises no formaldehyde or smaller amounts thereof than the part-formaldehyde-loaded aqueous solution I, use is made of water.

Generally, the various absorption stages are integrated in one absorption tower.

Expediently, the Brönsted base is added to the partial stream III in the form of a dilute solution, preferably in the form of dilute sodium hydroxide solution.

The solutions prepared in this manner preferably comprise from 10 to 50 ppm by weight of formaldehyde.

They have the advantage that, in them, tetroxane is formed only very slowly.

The low tetroxane content has a particularly favorable effect if these solutions are used to prepare 1,4-butanediol. In this case, a procedure is followed such that the aqueous solutions are reacted with acetylene, according to generally known processes, to form 1,4-butynediol and the 1,4-butynediol is subsequently hydrogenated to form 1,4-butanediol.

EXAMPLES

Example 1

Approximately 2 ml of a 0.1 molar sodium hydroxide solution were added to 100 ml of an aqueous formaldehyde solution comprising 49% by weight of formaldehyde, 1.25% by weight of methanol and 150 ppm of formic acid and the mixture was stored for a plurality of days at 60° C. The tetroxane content was measured daily (time of sodium hydroxide solution addition=zero day value)

Comparative Example

The procedure as described in Example 1 was followed, but, before the beginning of storage, sodium hydroxide solution was not added to the solution.

The result can be taken from Table 1.

TABLE 1

| | Tetroxane content [ppm] | |
|---|---|---|
| Days | Example 1 | Comparative example |
| 0 | 220 | 220 |
| 1 | 230 | 330 |
| 2 | 210 | 400 |
| 3 | 270 | 500 |

We claim:

1. A process for preparing an aqueous-formaldehyde solution comprising, absorbing a formaldehyde-loaded gas stream, in an absorption zone, in an aqueous solution comprising from 0.001% to 0.01% by weight of a Brönsted base, based on the formaldehyde absorbed, wherein said aqueous-formaldehyde solution comprises
   a) from 10 to 75% by weight of formaldehyde,
   b) from 0 to 500 ppm by weight of tetroxane,
   c) from 50 to 400 ppm by weight of formic acid, based on the formaldehyde absorbed; and
   d) from 0.2 to 5.0% by weight of methanol, based on the formaldehyde absorbed.

2. The process as claimed in claim 1, wherein said aqueous-formaldehyde solution has a pH of from 3.4 to 4.2.

3. A process for forming an aqueous-formaldehyde solution comprising, continuously,
   in a 1st absorption stage
      forming a part-formaldehyde-loaded aqueous solution II and a formaldehyde-depleted gas stream II having decreased formaldehyde content, by conducting a part-formaldehyde-depleted gas stream I and a part formaldehyde-loaded aqueous solution I in countercurrent through an absorption zone I, to partially absorb said part-formaldehyde-depleted gas stream I in said part-formaldehyde-loaded aqueous solution I,
      removing said formaldehyde-depleted gas stream II and said part-formaldehyde-loaded aqueous solution II from said absorption zone I,
      dividing said part-formaldehyde-loaded aqueous solution II into 2 partial streams I and II,
      passing said partial stream I into said absorption zone I together with an aqueous solution W which comprises no formaldehyde or smaller amounts thereof than said part-formaldehyde-loaded aqueous solution I to form said part-formaldehyde-loaded aqueous solution I,
   and in a further upstream absorption stage 2
      forming a formaldehyde-loaded aqueous solution IV, wherein said formaldehyde-loaded aqueous solution IV is an aqueous solution comprising,
      a) from 10 to 75% by weight of formaldehyde,
      b) from 0 to 500 ppm by weight of tetroxane,
      c) from 50 to 400 ppm by weight of formic acid, based on the formaldehyde absorbed; and
      d) from 0.2 to 5.0% by weight of methanol, based on the formaldehyde absorbed;

and said part-formaldehyde-depleted gas stream I by conducting a formaldehyde-loaded gas stream III and a part-formaldehyde-loaded aqueous solution III in countercurrent through an absorption zone II, to partially absorb said part-formaldehyde-depleted gas stream I in said part-formaldehyde-loaded aqueous solution I, removing said formaldehyde-loaded aqueous solution IV and said part-formaldehyde-depleted gas stream I from said absorption zone II, dividing said formaldehyde-loaded aqueous solution IV into 2 partial streams III and IV, producing a partial stream V by adding from 0.001 to 0.01% by weight of a Brönsted base to said partial stream III per part by weight of formaldehyde which is passed into said absorption zone II in the form of said formaldehyde-loaded gas stream III and forming said part-formaldehyde-loaded aqueous solution III by passing said partial stream V and said partial stream II together into said absorption zone II.

4. The process as claimed in claim 3, wherein said formaldehyde-loaded aqueous solution IV has a pH of from 3.4 to 4.2.

5. A process as claimed in claim 3, wherein 2 or 3 absorption stages of the first absorption stage type are connected in series and, in the last absorption stage, as aqueous solution which comprises no formaldehyde or smaller amounts thereof than the part-formaldehyde-loaded aqueous solution I, use is made of water.

6. A process as claimed in any one of claims 1, 3, or 5, wherein said Brönsted base is selected from the group consisting of ammonia, an alkali metal hydroxide or an alkali metal carbonate.

7. A process as claimed in any one of claims 1, 3, or 5, wherein said formaldehyde-loaded gas stream comprises from 5 to 30% by weight of formaldehyde
from 0.5 to 2.0% by weight of methanol
from 30 to 55% by weight of nitrogen.

* * * * *

UNITED STATES PATENT AND TRADEMARK OFFICE
CERTIFICATE OF CORRECTION

PATENT NO. : 6,471,928 B1  Page 1 of 1
DATED : October 29, 2002
INVENTOR(S) : Danz et al.

It is certified that error appears in the above-identified patent and that said Letters Patent is hereby corrected as shown below:

<u>Title page,</u>
Item [87], should read:

-- [87]  PCT Pub. No.: WO00/24699
         PCT Pub. Date: May 4, 2000 --

Signed and Sealed this

Eighteenth Day of March, 2003

JAMES E. ROGAN
*Director of the United States Patent and Trademark Office*